(12) United States Patent
Stotz et al.

(10) Patent No.: US 12,178,554 B2
(45) Date of Patent: Dec. 31, 2024

(54) SYSTEMS AND METHODS FOR DETERMINING A VISCOSITY OF A FLUID

(71) Applicant: KARDION GMBH, Stuttgart (DE)

(72) Inventors: Ingo Stotz, Ditzingen (DE); Thomas Alexander Schlebusch, Renningen (DE)

(73) Assignee: KARDION GMBH, Stuttgart (DE)

( * ) Notice: Subject to any disclaimer, the term of this patent is extended or adjusted under 35 U.S.C. 154(b) by 735 days.

(21) Appl. No.: 15/734,519

(22) PCT Filed: Jun. 6, 2019

(86) PCT No.: PCT/EP2019/064808
§ 371 (c)(1),
(2) Date: Jul. 20, 2021

(87) PCT Pub. No.: WO2019/234167
PCT Pub. Date: Dec. 12, 2019

(65) Prior Publication Data
US 2022/0047173 A1    Feb. 17, 2022

(30) Foreign Application Priority Data
Jun. 6, 2018 (DE) .......................... 102018208936.1

(51) Int. Cl.
*A61B 5/02* (2006.01)
*A61B 5/00* (2006.01)
(Continued)

(52) U.S. Cl.
CPC ........ *A61B 5/02035* (2013.01); *A61B 5/0215* (2013.01); *A61B 5/7246* (2013.01);
(Continued)

(58) Field of Classification Search
CPC . A61B 5/02035; A61B 5/0215; A61B 5/7246; A61B 8/488; A61M 60/531;
(Continued)

(56) References Cited

U.S. PATENT DOCUMENTS

| 3,088,323 A | 5/1963 | Welkowitz et al. |
| 4,023,562 A | 5/1977 | Hynecek et al. |

(Continued)

FOREIGN PATENT DOCUMENTS

| CA | 3122415 A1 * | 7/2020 | ............ A61M 60/13 |
| CN | 1192351 A | 9/1998 | |

(Continued)

OTHER PUBLICATIONS

Simon et al.; "Identification of Fluidic Element Models to Simulate the Short-Term Baroreflex§"; Proceedings of the 45th IEEE Conference on Decision & Control (2006) pp. 6738-6743.*

(Continued)

*Primary Examiner* — Dixomara Vargas
(74) *Attorney, Agent, or Firm* — Knobbe, Martens, Olson & Bear, LLP

(57) ABSTRACT

The approach presented here relates to a determination appliance (100) for determining a viscosity of a fluid. The determination appliance (100) has at least one determination device (110) and a provisioning device (115). The determination device (110) is designed to determine the viscosity of the fluid and/or a rotational speed (ω) of a blade wheel (205) for conveying the fluid by using at least one detected volume flow of the fluid and a detected pressure difference of the fluid. The provisioning device (115) is designed to provide or send a viscosity signal (130) representing the viscosity determined by the determination device (110).

18 Claims, 3 Drawing Sheets

(51) Int. Cl.
  *A61B 5/0215* (2006.01)
  *A61B 8/08* (2006.01)
  *A61M 60/178* (2021.01)
  *A61M 60/216* (2021.01)
  *A61M 60/403* (2021.01)
  *A61M 60/523* (2021.01)
  *A61M 60/531* (2021.01)

(52) U.S. Cl.
  CPC .......... *A61B 8/488* (2013.01); *A61M 60/178* (2021.01); *A61M 60/216* (2021.01); *A61M 60/403* (2021.01); *A61M 60/523* (2021.01); *A61M 60/531* (2021.01); *A61M 2205/3331* (2013.01); *A61M 2205/3365* (2013.01); *A61M 2205/3375* (2013.01); *A61M 2205/3379* (2013.01)

(58) Field of Classification Search
  CPC .............. A61M 60/178; A61M 60/403; A61M 60/216; A61M 2205/3331; A61M 2205/3365; A61M 2205/3375; A61M 2205/3379
  See application file for complete search history.

(56) References Cited

U.S. PATENT DOCUMENTS

| | | |
|---|---|---|
| 4,559,952 A | 12/1985 | Angelsen et al. |
| 4,781,525 A * | 11/1988 | Hubbard ............... A61M 60/38 417/63 |
| 4,888,011 A | 12/1989 | Kung et al. |
| 4,889,131 A | 12/1989 | Salem et al. |
| 4,902,272 A | 2/1990 | Milder et al. |
| 5,045,051 A | 9/1991 | Milder et al. |
| 5,269,811 A | 12/1993 | Hayes |
| 5,289,821 A | 3/1994 | Swartz |
| 5,456,715 A | 10/1995 | Liotta |
| 5,527,159 A | 6/1996 | Bozeman, Jr. et al. |
| 5,581,038 A | 12/1996 | Lampropoulos |
| 5,613,935 A | 3/1997 | Jarvik |
| 5,662,115 A | 9/1997 | Torp |
| 5,676,651 A | 10/1997 | Larson, Jr. et al. |
| 5,720,771 A | 2/1998 | Snell |
| 5,752,976 A | 5/1998 | Duffin et al. |
| 5,766,207 A | 6/1998 | Potter et al. |
| 5,827,203 A | 10/1998 | Nita |
| 5,888,242 A | 3/1999 | Antaki et al. |
| 5,904,708 A | 5/1999 | Goedeke |
| 5,911,685 A | 6/1999 | Siess et al. |
| 5,964,694 A | 10/1999 | Siess et al. |
| 5,980,465 A | 11/1999 | Elgas |
| 6,007,478 A | 12/1999 | Siess et al. |
| 6,024,704 A | 2/2000 | Meador et al. |
| 6,053,873 A | 4/2000 | Govari et al. |
| 6,176,822 B1 | 1/2001 | Nix et al. |
| 6,183,412 B1 | 2/2001 | Benkowsi et al. |
| 6,185,460 B1 | 2/2001 | Thompson |
| 6,190,324 B1 | 2/2001 | Kieval et al. |
| 6,210,318 B1 | 4/2001 | Lederman |
| 6,231,498 B1 | 5/2001 | Pfeiffer et al. |
| 6,245,007 B1 | 6/2001 | Bedingham et al. |
| 6,314,322 B1 | 11/2001 | Rosenberg |
| 6,351,048 B1 | 2/2002 | Schob et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,512,949 B1 | 1/2003 | Combs et al. |
| 6,530,876 B1 | 3/2003 | Spence |
| 6,540,658 B1 | 4/2003 | Fasciano et al. |
| 6,540,659 B1 | 4/2003 | Milbocker |
| 6,561,975 B1 | 5/2003 | Pool et al. |
| 6,579,257 B1 | 6/2003 | Elgas et al. |
| 6,602,182 B1 | 8/2003 | Milbocker |
| 6,605,032 B2 | 8/2003 | Benkowsi et al. |
| 6,652,447 B2 | 11/2003 | Benkowsi et al. |
| 6,731,976 B2 | 5/2004 | Penn et al. |
| 6,879,126 B2 | 4/2005 | Paden et al. |
| 6,912,423 B2 | 6/2005 | Ley et al. |
| 6,949,066 B2 | 9/2005 | Bearnson et al. |
| 6,984,201 B2 | 1/2006 | Khaghani et al. |
| 7,022,100 B1 | 4/2006 | Aboul-Hosn et al. |
| 7,024,244 B2 | 4/2006 | Muhlenberg et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,396,327 B2 | 7/2008 | Morello |
| 7,513,864 B2 | 4/2009 | Kantrowitz et al. |
| 7,520,850 B2 | 4/2009 | Brockway |
| 7,591,777 B2 | 9/2009 | LaRose |
| 7,744,560 B2 | 6/2010 | Struble |
| 7,794,384 B2 | 9/2010 | Sugiura et al. |
| 7,819,916 B2 | 10/2010 | Yaegashi |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,951,062 B2 | 5/2011 | Morello |
| 7,951,129 B2 | 5/2011 | Chinchoy |
| 7,963,905 B2 | 6/2011 | Salmonsen et al. |
| 7,988,728 B2 | 8/2011 | Ayre |
| 8,075,472 B2 | 12/2011 | Zilbershlag et al. |
| 8,190,390 B2 | 5/2012 | Morello et al. |
| 8,211,028 B2 | 7/2012 | Karamanoglu et al. |
| 8,303,482 B2 | 11/2012 | Schima et al. |
| 8,323,173 B2 | 12/2012 | Benkowsi et al. |
| 8,435,182 B1 | 5/2013 | Tamura |
| 8,449,444 B2 | 5/2013 | Poirier |
| 8,545,380 B2 | 10/2013 | Farnan et al. |
| 8,585,572 B2 | 11/2013 | Mehmanesh |
| 8,591,393 B2 | 11/2013 | Walters et al. |
| 8,594,790 B2 | 11/2013 | Kjellstrom et al. |
| 8,622,949 B2 | 1/2014 | Zafirelis et al. |
| 8,657,733 B2 | 2/2014 | Ayre et al. |
| 8,657,875 B2 | 2/2014 | Kung et al. |
| 8,715,151 B2 | 5/2014 | Poirier |
| 8,747,293 B2 | 6/2014 | Arndt et al. |
| 8,849,398 B2 | 9/2014 | Evans |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,897,873 B2 | 11/2014 | Schima et al. |
| 8,903,492 B2 | 12/2014 | Soykan et al. |
| 9,091,271 B2 | 7/2015 | Bourque |
| 9,297,735 B2 | 3/2016 | Graichen et al. |
| 9,308,305 B2 | 4/2016 | Chen et al. |
| 9,345,824 B2 | 5/2016 | Mohl et al. |
| 9,371,826 B2 | 6/2016 | Yanai et al. |
| 9,427,508 B2 | 8/2016 | Reyes et al. |
| 9,474,840 B2 | 10/2016 | Siess |
| 9,492,601 B2 | 11/2016 | Casas et al. |
| 9,511,179 B2 | 12/2016 | Casas et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,566,374 B2 | 2/2017 | Spence et al. |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,694,123 B2 | 7/2017 | Bourque et al. |
| 9,713,701 B2 | 7/2017 | Sarkar et al. |
| 9,744,282 B2 | 8/2017 | Rosenberg et al. |
| 9,833,550 B2 | 12/2017 | Siess |
| 9,848,899 B2 | 12/2017 | Sliwa et al. |
| 9,849,224 B2 | 12/2017 | Angwin et al. |
| 9,878,087 B2 | 1/2018 | Richardson et al. |
| 9,943,236 B2 | 4/2018 | Bennett et al. |

(56) References Cited

U.S. PATENT DOCUMENTS

| | | |
|---|---|---|
| 9,950,102 B2 | 4/2018 | Spence et al. |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,279,093 B2 | 5/2019 | Reichenbach et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,376,162 B2 | 8/2019 | Edelman et al. |
| 10,413,651 B2 | 9/2019 | Yomtov et al. |
| 10,426,879 B2 | 10/2019 | Farnan |
| 10,449,275 B2 | 10/2019 | Corbett |
| 10,500,322 B2 | 12/2019 | Karch |
| 10,525,178 B2 | 1/2020 | Zeng |
| 10,549,020 B2 | 2/2020 | Spence et al. |
| 10,561,771 B2 | 2/2020 | Heilman et al. |
| 10,561,772 B2 | 2/2020 | Schumacher |
| 10,561,773 B2 | 2/2020 | Ferrari et al. |
| 10,632,241 B2 | 4/2020 | Schenck et al. |
| 10,660,998 B2 | 5/2020 | Hodges |
| 10,668,195 B2 | 6/2020 | Flores |
| 10,732,583 B2 | 8/2020 | Rudser |
| 10,857,275 B2 | 12/2020 | Granegger |
| 11,027,114 B2 | 6/2021 | D'Ambrosio et al. |
| RE48,649 E | 7/2021 | Siess |
| 11,067,085 B2 | 7/2021 | Granegger et al. |
| 11,120,908 B2 | 9/2021 | Agnello et al. |
| 11,131,968 B2 | 9/2021 | Rudser |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,185,682 B2 | 11/2021 | Farnan |
| 11,191,945 B2 | 12/2021 | Siess et al. |
| 11,197,618 B2 | 12/2021 | Edelman et al. |
| 11,217,344 B2 | 1/2022 | Agnello |
| 11,235,139 B2 | 2/2022 | Kudlik |
| 11,241,572 B2 | 2/2022 | Dague et al. |
| 11,273,299 B2 | 3/2022 | Wolman et al. |
| 11,285,310 B2 | 3/2022 | Curran et al. |
| 11,285,311 B2 | 3/2022 | Siess et al. |
| 11,298,524 B2 | 4/2022 | El Katerji et al. |
| 11,311,711 B2 | 4/2022 | Casas et al. |
| 11,316,679 B2 | 4/2022 | Agnello |
| 11,320,382 B2 | 5/2022 | Aikawa |
| 11,324,395 B2 | 5/2022 | Banik et al. |
| 11,331,082 B2 | 5/2022 | Itoh et al. |
| 11,337,724 B2 | 5/2022 | Masubuchi et al. |
| 11,338,125 B2 | 5/2022 | Liu et al. |
| 11,351,356 B2 | 6/2022 | Mohl |
| 11,351,357 B2 | 6/2022 | Mohl |
| 11,351,358 B2 | 6/2022 | Nix et al. |
| 11,357,438 B2 | 6/2022 | Stewart et al. |
| 11,357,968 B2 | 6/2022 | El Katerji et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,444 B2 | 8/2022 | Nix et al. |
| 11,413,445 B2 | 8/2022 | Brown et al. |
| 11,420,041 B2 | 8/2022 | Karch |
| 11,439,806 B2 | 9/2022 | Kimball et al. |
| 11,446,481 B2 | 9/2022 | Wolman et al. |
| 11,478,629 B2 | 10/2022 | Harjes et al. |
| 11,517,740 B2 | 12/2022 | Agarwa et al. |
| 11,521,723 B2 | 12/2022 | Liu et al. |
| 11,524,165 B2 | 12/2022 | Tan et al. |
| 11,527,322 B2 | 12/2022 | Agnello et al. |
| 11,529,062 B2 | 12/2022 | Moyer et al. |
| 11,554,260 B2 | 1/2023 | Reyes et al. |
| 11,572,879 B2 | 2/2023 | Mohl |
| 11,574,741 B2 | 2/2023 | Tan et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,587,337 B2 | 2/2023 | Lemay et al. |
| 11,590,337 B2 | 2/2023 | Granegger et al. |
| 11,622,695 B1 | 4/2023 | Adriola et al. |
| 11,628,293 B2 | 4/2023 | Gandhi et al. |
| 11,639,722 B2 | 5/2023 | Medvedev et al. |
| 11,648,386 B2 | 5/2023 | Poirer |
| 11,653,841 B2 | 5/2023 | Reyes et al. |
| 11,666,746 B2 | 6/2023 | Ferrari et al. |
| 11,668,321 B2 | 6/2023 | Richert et al. |
| 11,674,517 B2 | 6/2023 | Mohl |
| 11,676,718 B2 | 6/2023 | Agnello et al. |
| 11,684,276 B2 | 6/2023 | Cros et al. |
| 11,684,769 B2 | 6/2023 | Harjes et al. |
| 11,694,539 B2 | 7/2023 | Kudlik et al. |
| 11,694,813 B2 | 7/2023 | El Katerji et al. |
| 11,696,782 B2 | 7/2023 | Carlson et al. |
| 11,707,617 B2 | 7/2023 | Reyes et al. |
| 11,712,167 B2 | 8/2023 | Medvedev et al. |
| 11,754,077 B1 | 9/2023 | Mohl |
| D1,001,145 S | 10/2023 | Lussier et al. |
| D1,001,146 S | 10/2023 | Lussier et al. |
| 11,771,885 B2 | 10/2023 | Liu et al. |
| 11,779,234 B2 | 10/2023 | Harjes et al. |
| 11,781,551 B2 | 10/2023 | Yanai et al. |
| 11,790,487 B2 | 10/2023 | Barbato et al. |
| 11,793,994 B2 | 10/2023 | Josephy et al. |
| 11,806,116 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,818,782 B2 | 11/2023 | Doudian et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,837,364 B2 | 12/2023 | Lee et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,864,878 B2 | 1/2024 | Duval et al. |
| 11,872,384 B2 | 1/2024 | Cotter |
| 11,883,207 B2 | 1/2024 | El Katerji et al. |
| D1,014,552 S | 2/2024 | Lussier et al. |
| 11,890,082 B2 | 2/2024 | Cros et al. |
| 11,896,199 B2 | 2/2024 | Lent et al. |
| 11,900,660 B2 | 2/2024 | Saito et al. |
| 11,903,657 B2 | 2/2024 | Geric et al. |
| 11,906,411 B2 | 2/2024 | Graichen et al. |
| 11,911,550 B2 | 2/2024 | Itamochi et al. |
| D1,017,634 S | 3/2024 | Lussier et al. |
| D1,017,699 S | 3/2024 | Moore et al. |
| 11,923,078 B2 | 3/2024 | Fallen et al. |
| 11,923,093 B2 | 3/2024 | Moffitt et al. |
| 11,925,794 B2 | 3/2024 | Malkin et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,986,274 B2 | 5/2024 | Edelman |
| 12,017,076 B2 | 6/2024 | Tan et al. |
| 12,023,476 B2 | 7/2024 | Tuval et al. |
| 12,029,891 B2 | 7/2024 | Siess et al. |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2002/0147495 A1 | 10/2002 | Petroff |
| 2002/0151761 A1 | 10/2002 | Viole et al. |
| 2003/0069465 A1 | 4/2003 | Benkowski et al. |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2004/0022640 A1 | 2/2004 | Siess et al. |

(56) References Cited

U.S. PATENT DOCUMENTS

| | | |
|---|---|---|
| 2004/0044266 A1 | 3/2004 | Siess et al. |
| 2004/0065143 A1 | 4/2004 | Husher |
| 2004/0130009 A1 | 7/2004 | Tangpuz |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0241019 A1 | 12/2004 | Goldowsky |
| 2004/0260346 A1 | 12/2004 | Overall et al. |
| 2005/0001324 A1 | 1/2005 | Dunn |
| 2005/0019167 A1 | 1/2005 | Nusser et al. |
| 2005/0107658 A1 | 5/2005 | Brockway |
| 2005/0126268 A1 | 6/2005 | Ouriev et al. |
| 2005/0267322 A1 | 12/2005 | LaRose |
| 2006/0030809 A1 | 2/2006 | Barzilay et al. |
| 2006/0108697 A1 | 5/2006 | Wang |
| 2006/0108901 A1 | 5/2006 | Mao-Chin et al. |
| 2006/0122583 A1 | 6/2006 | Pesach et al. |
| 2006/0196277 A1 | 9/2006 | Allen et al. |
| 2006/0229488 A1 | 10/2006 | Ayre et al. |
| 2006/0287600 A1 | 12/2006 | McEowen |
| 2006/0287604 A1 | 12/2006 | Hickey |
| 2007/0060787 A1 | 3/2007 | Peters et al. |
| 2007/0073352 A1 | 3/2007 | Euler et al. |
| 2007/0088214 A1 | 4/2007 | Shuros et al. |
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2007/0299325 A1 | 12/2007 | Farrell et al. |
| 2008/0015517 A1 | 1/2008 | Geistert et al. |
| 2008/0082005 A1 | 4/2008 | Stern et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1* | 5/2008 | Weitzel ............... A61M 1/3656 |
| | | 210/741 |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0306328 A1 | 12/2008 | Ercolani |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1* | 4/2009 | Hekmat ............... A61B 5/6852 |
| | | 623/1.42 |
| 2009/0131765 A1 | 5/2009 | Roschak et al. |
| 2009/0204163 A1 | 8/2009 | Shuros et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0184301 A1 | 7/2011 | Holmstrom |
| 2011/0218435 A1 | 9/2011 | Srinivasan et al. |
| 2011/0230068 A1 | 9/2011 | Pahl |
| 2012/0022645 A1 | 1/2012 | Burke |
| 2012/0084024 A1 | 4/2012 | Norcross, Jr. |
| 2012/0150089 A1 | 6/2012 | Penka et al. |
| 2012/0203476 A1 | 8/2012 | Dam |
| 2012/0247200 A1 | 10/2012 | Ahonen et al. |
| 2012/0310037 A1 | 12/2012 | Choi et al. |
| 2012/0330214 A1* | 12/2012 | Peters ................. A61M 1/1603 |
| | | 604/6.11 |
| 2013/0041204 A1 | 2/2013 | Heilman et al. |
| 2013/0046129 A1 | 2/2013 | Medvedev et al. |
| 2013/0066141 A1 | 3/2013 | Doerr et al. |
| 2013/0072846 A1* | 3/2013 | Heide ..................... F04D 29/00 |
| | | 604/6.11 |
| 2013/0116575 A1 | 5/2013 | Mickle et al. |
| 2013/0144379 A1 | 6/2013 | Najafi et al. |
| 2013/0289376 A1 | 10/2013 | Lang |
| 2013/0303831 A1 | 11/2013 | Evans |
| 2014/0005467 A1 | 1/2014 | Farnan et al. |
| 2014/0013852 A1 | 1/2014 | Brown et al. |
| 2014/0100414 A1 | 4/2014 | Tamez et al. |
| 2014/0114202 A1 | 4/2014 | Hein et al. |
| 2014/0128659 A1 | 5/2014 | Heuring et al. |
| 2014/0200389 A1 | 7/2014 | Yanai et al. |
| 2014/0243688 A1 | 8/2014 | Caron et al. |
| 2014/0275720 A1 | 9/2014 | Ferrari |
| 2014/0296677 A1 | 10/2014 | McEowen |
| 2014/0303426 A1 | 10/2014 | Kerkhoffs et al. |
| 2014/0342203 A1 | 11/2014 | Elian |
| 2015/0032007 A1 | 1/2015 | Ottevanger et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1* | 10/2015 | Muller ................. A61M 60/174 |
| | | 600/16 |
| 2015/0306290 A1 | 10/2015 | Rosenberg et al. |
| 2015/0306291 A1 | 10/2015 | Bonde et al. |
| 2015/0307344 A1 | 10/2015 | Ernst |
| 2015/0327921 A1 | 11/2015 | Govari |
| 2015/0335804 A1 | 11/2015 | Marseille et al. |
| 2015/0365738 A1 | 12/2015 | Purvis et al. |
| 2016/0000983 A1* | 1/2016 | Mohl ..................... A61M 60/17 |
| | | 600/16 |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0045165 A1 | 2/2016 | Braido et al. |
| 2016/0095968 A1 | 4/2016 | Rudser |
| 2016/0101230 A1 | 4/2016 | Ochsner et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0250399 A1 | 9/2016 | Tiller et al. |
| 2016/0278856 A1 | 9/2016 | Panescu |
| 2016/0338629 A1 | 11/2016 | Doerr |
| 2017/0010144 A1 | 1/2017 | Lenner et al. |
| 2017/0021070 A1 | 1/2017 | Petersen |
| 2017/0049945 A1 | 2/2017 | Halvorsen et al. |
| 2017/0086780 A1 | 3/2017 | Sokulin et al. |
| 2017/0098491 A1 | 4/2017 | Ziaie et al. |
| 2017/0112985 A1 | 4/2017 | Yomtov |
| 2017/0128646 A1 | 5/2017 | Karch |
| 2017/0136164 A1 | 5/2017 | Yeatts |
| 2017/0202575 A1 | 7/2017 | Stanfield et al. |
| 2017/0224279 A1 | 8/2017 | Cahan et al. |
| 2017/0239407 A1 | 8/2017 | Hayward |
| 2017/0258960 A1* | 9/2017 | Katsuki ............... A61M 60/109 |
| 2017/0348470 A1 | 12/2017 | D'Ambrosio et al. |
| 2017/0354812 A1 | 12/2017 | Callaghan et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0110910 A1* | 4/2018 | Rodemerk .......... A61M 60/148 |
| 2018/0199635 A1 | 7/2018 | Longinotti-Buitoni et al. |
| 2018/0250457 A1 | 9/2018 | Morello et al. |
| 2018/0256796 A1 | 9/2018 | Hansen |
| 2018/0256800 A1 | 9/2018 | Conyers et al. |
| 2018/0264182 A1 | 9/2018 | Spanier et al. |

(56) References Cited

U.S. PATENT DOCUMENTS

| | | | |
|---|---|---|---|
| 2018/0280598 A1* | 10/2018 | Curran | A61B 5/02141 |
| 2018/0316209 A1 | 11/2018 | Gliner | |
| 2018/0326131 A1 | 11/2018 | Muller et al. | |
| 2018/0353667 A1 | 12/2018 | Moyer et al. | |
| 2018/0369469 A1 | 12/2018 | Le Duc De Lillers et al. | |
| 2019/0001038 A1 | 1/2019 | Yomtov et al. | |
| 2019/0054223 A1 | 2/2019 | Frazier et al. | |
| 2019/0083690 A1 | 3/2019 | Siess et al. | |
| 2019/0192752 A1 | 6/2019 | Tiller et al. | |
| 2019/0192753 A1 | 6/2019 | Liu et al. | |
| 2019/0209755 A1 | 7/2019 | Nix et al. | |
| 2019/0209758 A1 | 7/2019 | Tuval et al. | |
| 2019/0216995 A1 | 7/2019 | Kapur et al. | |
| 2019/0217002 A1* | 7/2019 | Urakabe | A61M 1/3639 |
| 2019/0223877 A1 | 7/2019 | Nitzen et al. | |
| 2019/0240680 A1* | 8/2019 | Hayakawa | B04B 11/02 |
| 2019/0254543 A1 | 8/2019 | Hartholt et al. | |
| 2019/0282741 A1* | 9/2019 | Franano | A61M 60/816 |
| 2019/0282744 A1 | 9/2019 | D'Ambrosio et al. | |
| 2019/0351117 A1 | 11/2019 | Cambronne et al. | |
| 2019/0351118 A1 | 11/2019 | Graichen et al. | |
| 2020/0016309 A1 | 1/2020 | Kallenbach et al. | |
| 2020/0038567 A1 | 2/2020 | Siess et al. | |
| 2020/0060559 A1 | 2/2020 | Edelman et al. | |
| 2020/0069857 A1 | 3/2020 | Schwammenthal et al. | |
| 2020/0147283 A1 | 5/2020 | Tanner et al. | |
| 2020/0164125 A1 | 5/2020 | Muller et al. | |
| 2020/0164126 A1 | 5/2020 | Muller | |
| 2020/0253583 A1 | 8/2020 | Brisken et al. | |
| 2020/0312450 A1 | 10/2020 | Agnello et al. | |
| 2021/0268264 A1 | 9/2021 | Stotz | |
| 2021/0290087 A1 | 9/2021 | Schlebusch | |
| 2021/0290930 A1* | 9/2021 | Kassel | A61M 60/237 |
| 2021/0290933 A1 | 9/2021 | Stotz | |
| 2021/0339002 A1 | 11/2021 | Schlebusch et al. | |
| 2021/0339004 A1 | 11/2021 | Schlebusch et al. | |
| 2021/0346674 A1 | 11/2021 | Baumbach et al. | |
| 2021/0346675 A1 | 11/2021 | Schlebusch et al. | |
| 2021/0346676 A1 | 11/2021 | Schlebusch et al. | |
| 2021/0346677 A1 | 11/2021 | Baumbach et al. | |
| 2021/0346678 A1 | 11/2021 | Baumbach et al. | |
| 2021/0378523 A1 | 12/2021 | Budde | |
| 2021/0379359 A1 | 12/2021 | Schellenberg | |
| 2021/0379360 A1 | 12/2021 | Schellenberg | |
| 2021/0393944 A1 | 12/2021 | Wenning | |
| 2022/0016411 A1 | 1/2022 | Winterwerber | |
| 2022/0032032 A1 | 2/2022 | Schlebusch et al. | |
| 2022/0032036 A1 | 2/2022 | Baumbach et al. | |
| 2022/0039669 A1 | 2/2022 | Schlebusch et al. | |
| 2022/0050037 A1* | 2/2022 | Stotz | A61B 5/14503 |
| 2022/0072298 A1 | 3/2022 | Spanier et al. | |
| 2022/0076807 A1 | 3/2022 | Agnello | |
| 2022/0079457 A1 | 3/2022 | Tuval et al. | |
| 2022/0105339 A1 | 4/2022 | Nix et al. | |
| 2022/0126085 A1 | 4/2022 | Farnan | |
| 2022/0126086 A1 | 4/2022 | Schlebusch et al. | |
| 2022/0142462 A1* | 5/2022 | Douk | A61B 1/015 |
| 2022/0161019 A1 | 5/2022 | Mitze et al. | |
| 2023/0173250 A1* | 6/2023 | Stigloher | G01S 17/58 |
| | | | 600/17 |
| 2023/0191141 A1 | 6/2023 | Wenning et al. | |
| 2024/0011808 A1 | 1/2024 | Winzer et al. | |
| 2024/0074828 A1 | 3/2024 | Wenning | |
| 2024/0245902 A1 | 7/2024 | Schlebusch et al. | |

FOREIGN PATENT DOCUMENTS

| | | |
|---|---|---|
| CN | 1222862 A | 7/1999 |
| CN | 1202871 C | 5/2005 |
| CN | 1661338 A | 8/2005 |
| CN | 101128168 | 2/2008 |
| CN | 101208045 | 6/2008 |
| CN | 101214158 | 7/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201658687 | 12/2010 |
| CN | 102421372 | 4/2012 |
| CN | 102803923 | 11/2012 |
| CN | 103328018 | 9/2013 |
| CN | 103857326 | 6/2014 |
| CN | 103957957 | 7/2014 |
| CN | 104105449 | 10/2014 |
| CN | 104188687 | 12/2014 |
| CN | 106104229 | 11/2016 |
| CN | 106333707 | 1/2017 |
| CN | 206007680 | 3/2017 |
| CN | 107530479 | 1/2018 |
| CN | 107632167 | 1/2018 |
| CN | 109939282 | 6/2019 |
| CN | 209790495 | 12/2019 |
| CN | 210020563 | 2/2020 |
| DE | 195 20 920 | 12/1995 |
| DE | 198 21 307 | 10/1999 |
| DE | 100 59 714 | 5/2002 |
| DE | 100 60 275 | 6/2002 |
| DE | 101 44 269 | 3/2003 |
| DE | 102 26 305 | 10/2003 |
| DE | 10 2006 001 180 | 9/2007 |
| DE | 10 2009 007 216 | 8/2010 |
| DE | 10 2009 011 726 | 9/2010 |
| DE | 10 2009 025 464 | 1/2011 |
| DE | 10 2009 047 845 | 3/2011 |
| DE | 10 2011 106 142 | 12/2012 |
| DE | 20 2011 110 389 | 9/2013 |
| DE | 10 2015 004 177 | 10/2015 |
| DE | 10 2015 219 263 | 4/2017 |
| DE | 10 2015 222 199 | 5/2017 |
| DE | 20 2015 009 422 | 7/2017 |
| DE | 10 2012 207 042 | 9/2017 |
| DE | 10 2016 013 334 | 4/2018 |
| DE | 10 2018 208 536 | 12/2019 |
| DE | 10 2018 208 862 | 12/2019 |
| DE | 10 2018 208 916 | 12/2019 |
| DE | 10 2018 208 927 | 12/2019 |
| DE | 10 2018 208 945 | 12/2019 |
| DE | 10 2018 210 076 | 12/2019 |
| DE | 10 2018 212 153 | 1/2020 |
| DE | 10 2018 213 151 | 2/2020 |
| DE | 10 2018 213 350 | 2/2020 |
| DE | 10 2018 220 658 | 6/2020 |
| DE | 10 2018 222 505 | 6/2020 |
| DE | 10 2020 102 473 | 8/2021 |
| DE | 11 2020 003 151 | 3/2022 |
| EP | 0 794 411 | 9/1997 |
| EP | 0 916 359 | 5/1999 |
| EP | 1 062 959 | 12/2000 |
| EP | 1 339 443 | 11/2001 |
| EP | 1 011 803 | 9/2004 |
| EP | 1 354 606 | 6/2006 |
| EP | 2 143 385 | 1/2010 |
| EP | 2 175 770 | 4/2010 |
| EP | 2 187 807 | 6/2012 |
| EP | 2 570 143 | 3/2013 |
| EP | 2 401 003 | 10/2013 |
| EP | 1 871 441 | 11/2014 |
| EP | 2 859 911 | 4/2015 |
| EP | 2 213 227 | 8/2016 |
| EP | 2 835 141 | 8/2016 |
| EP | 3 088 016 | 11/2016 |
| EP | 2 585 129 | 3/2017 |
| EP | 2 945 661 | 11/2017 |
| EP | 2 136 861 | 12/2017 |
| EP | 3 020 426 | 12/2017 |
| EP | 3 287 154 | 2/2018 |
| EP | 3 205 359 | 8/2018 |
| EP | 3 205 360 | 8/2018 |
| EP | 3 389 738 | 8/2019 |
| EP | 2 505 090 | 12/2019 |
| EP | 3 668 560 | 6/2020 |

(56) References Cited

FOREIGN PATENT DOCUMENTS

| | | |
|---|---|---|
| EP | 3 720 520 | 10/2020 |
| EP | 3 753 594 | 12/2020 |
| EP | 3 357 523 | 1/2021 |
| EP | 3 490 628 | 2/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 3 131 600 | 6/2021 |
| EP | 3 131 615 | 6/2021 |
| EP | 3 463 505 | 9/2021 |
| EP | 3 884 970 | 9/2021 |
| EP | 2 599 510 | 10/2021 |
| EP | 3 003 421 | 10/2021 |
| EP | 3 027 241 | 10/2021 |
| EP | 3 668 561 | 10/2021 |
| EP | 3 164 168 | 12/2021 |
| EP | 3 344 129 | 12/2021 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 984 589 | 4/2022 |
| EP | 3 654 006 | 5/2022 |
| EP | 3 737 310 | 7/2022 |
| EP | 2 999 400 | 8/2022 |
| EP | 3 711 788 | 8/2022 |
| EP | 3 694 573 | 9/2022 |
| EP | 3 600 477 | 10/2022 |
| EP | 3 897 768 | 10/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 685 562 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 970 765 | 7/2024 |
| ES | 2913485 T3 * | 6/2022 ........... A61B 5/0031 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2012-520157 | 9/2012 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2019-523110 | 8/2019 |
| JP | 2020-072985 | 5/2020 |
| WO | WO 92/015239 | 9/1992 |
| WO | WO 98/043688 | 10/1998 |
| WO | WO 00/033047 | 6/2000 |
| WO | WO 2006/122001 | 11/2006 |
| WO | WO 2010/142286 | 12/2010 |
| WO | WO 2010/143272 | 12/2010 |
| WO | WO 2012/018917 | 2/2012 |
| WO | WO 2012/112378 | 8/2012 |
| WO | WO 2013/160443 | 10/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2016/001284 | 1/2016 |
| WO | WO 2016/066180 | 5/2016 |
| WO | WO 2016/137743 | 9/2016 |
| WO | WO 2017/032751 | 3/2017 |
| WO | WO 2017/066257 | 4/2017 |
| WO | WO 2017/106190 | 6/2017 |
| WO | WO 2017/147291 | 8/2017 |
| WO | WO 2017/214118 | 12/2017 |
| WO | WO 2018/048800 | 3/2018 |
| WO | WO 2018/109038 | 6/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/078723 | 4/2019 |
| WO | WO 2019/126721 | 6/2019 |
| WO | WO 2019/137911 | 7/2019 |
| WO | WO 2019/193604 | 10/2019 |
| WO | WO 2019/219883 | 11/2019 |
| WO | WO 2019/229210 | 12/2019 |

(56) References Cited

FOREIGN PATENT DOCUMENTS

| WO | WO 2019/229220 | 12/2019 |
| --- | --- | --- |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/243582 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2022/074136 | 4/2022 |
| WO | WO 2022/109590 | 5/2022 |
| WO | WO 2022/173970 | 8/2022 |
| WO | WO 2023/049813 | 3/2023 |

OTHER PUBLICATIONS

R. Lombardi et al.; "Flow Rate Profiler: an instrument to measure blood velocity profiles"; Ultrasonics 39 (2001) pp. 143-150.*

Hertz Ph.D. et al, "Ultrasonic Engineering in Heart Diagnosis", The American Journal of Cardiology, Jan. 1967, vol. 19, No. 1, pp. 6-17.

International Preliminary Report on Patentability and Written Opinion received in PCT Application No. PCT/EP2019/064808, dated Sep. 29, 2020 in 34 pages.

International Search Report and Written Opinion received in PCT Application No. PCT/EP2019/064808, dated Aug. 28, 2019 in 17 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

"Understanding Hot-Wire Anemometry", Advanced Thermal Solutions, Inc., 2007, pp. 13-17.

Yuanyuan et al., "Characteristics Analysis for Doppler Ultrasound Blood Flow Signals", China Medical Device Information, 5(1), Feb. 28, 1999, pp. 36-42.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

Zhang, Dabiao et al., "Design of Microwave Velocity and Distance Monitor System", Instrument Technique and Sensor, Hebei Normal University, Apr. 25, 2004, pp. 3.

Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.

* cited by examiner

SYSTEMS AND METHODS FOR DETERMINING A VISCOSITY OF A FLUID

BACKGROUND

Field

The invention relates to a determination appliance and to a method for determining a viscosity of a fluid. The invention also relates to a computer program and to a machine-readable storage medium on which the computer program is stored.

Description of the Related Art

PT (prothrombin time) and INR (international normalized ratio) are the standard measure for blood coagulation. Usually, the INR in blood samples is determined by adding thromboplastin and subsequently measuring the time to coagulation. The determination can take place in the laboratory; today, test strip devices are also available for self-measurement by the patient, comparable to the procedure of a blood sugar measurement. For patients with heart support systems, so-called coagulation management is essential for minimizing pump thromboses. Monitoring of blood viscosity as an INR replacement parameter may be sufficient for coagulation management.

EP 2 175 770 B1 describes an explicit blood viscosity sensor on the basis of surface acoustic waves, SAW for short, for determining viscosity.

U.S. Pat. No. 7,591,777 B2 describes a viscosity determination in heart support systems by means of the mechanical effect of the blood viscosity on the drive of the heart support system.

SUMMARY

The object of the invention is to specify an improved method for determining a viscosity of a fluid and an improved determination appliance for this purpose. It is in particular an object of the invention to specify a method and an appliance that allows the continuous determination of the viscosity of a fluid on a short time scale.

This object is achieved by the determination appliance and systems and methods disclosed herein. Advantageous embodiments of the invention are also disclosed herein.

In the following, a determination appliance for determining a viscosity of a fluid and a method according to the invention for determining a viscosity of a fluid and, lastly, a corresponding computer program are presented. Advantageous developments and improvements of the objects specified in the independent claims are possible by means of the measures listed in the dependent claims.

The advantages achievable with the presented approach are that a determination appliance presented here is designed to quickly and easily determine and provide or send the viscosity of a fluid by using current flow parameters of the fluid.

A determination appliance for determining a viscosity of a fluid is presented. The determination appliance has at least one determination device and a provisioning device. The determination device is designed to determine the viscosity of the fluid by using at least one detected volume flow of the fluid and a detected pressure difference of the fluid and/or a rotational speed of a blade wheel for conveying the fluid. The provisioning device is designed to provide or send a viscosity signal that represents the viscosity determined by the determination device.

The determination device can be designed to determine the viscosity by using a functional relationship between the volume flow and the pressure difference to the viscosity and/or by using a lookup table, wherein a relationship between the volume flow and the pressure difference to the viscosity can in particular be stored in the lookup table. Thus, by using the detected volume flow and the detected pressure difference, a viscosity assigned to these values can be read quickly and easily from the lookup table. Or, by using the detected volume flow and the detected pressure difference, the viscosity can be determined quickly and easily by solving the functional relationship. In order to create the lookup table, a calibration of a measurement can, for example, be carried out or may have been carried out in advance such that both the viscosity varies in the relevant range and a rotational speed of, for example, a pump device for conveying the fluid varies in the relevant range, and the resulting pump flows are or were measured. Alternatively or additionally, on the basis of the calibration values, an empirical function, for example, can be determined or may have been determined, with the help of which the viscosity can subsequently be calculated. The lookup table and/or the functional relationship can be stored in the determination device or can be read by the determination device for use.

The determination device can, for example, also be arranged outside the body of a patient in order to determine the viscosity of the fluid data such as the aforementioned detected volume flow of the fluid and a detected pressure difference of the fluid and/or a rotational speed of a pump. For this purpose, the determination device can then, for example, obtain the values or parameters that are required for the determination of the viscosity wirelessly or via a signal line so that it can also determine the viscosity of the fluid outside the body of the patient.

The determination appliance can have a cannula with a receiving interface for receiving the fluid and a discharge interface opposite the receiving interface for discharging the fluid, wherein the pressure difference can in particular represent a difference between a pressure of the fluid in the region of the receiving interface and a further pressure of the fluid in the region of the discharge interface and/or the volume flow can represent a volume flow of the fluid through the cannula. Such a cannula can be formed for use on or in a heart support system. For example, the cannula can be formed or designed to receive blood as the fluid. The current viscosity of the blood in the cannula can thus be advantageously determined by using the determination appliance.

It is furthermore advantageous when the determination appliance has, according to one embodiment, a blade wheel for conveying the fluid from the receiving interface to the discharge interface of the cannula, wherein the blade wheel is arranged or can be arranged in particular on or in the region of the discharge interface. The blade wheel can be arranged, for example, in a discharge section adjacent to the discharge interface. The volume flow of the fluid and the pressure difference can thus be effected during operation of the blade wheel.

In this case, it is advantageous for the determination appliance to have a volume flow sensor, which is designed to detect a volume flow of the fluid through the cannula and to provide or send it to the determination device, wherein the volume flow sensor is in particular arranged in the region of the receiving interface. A current volume flow can thus be taken into account to determine the viscosity.

This volume flow sensor can have at least one Doppler sensor for detecting Doppler ultrasound and/or a thermofilament anemometry sensor and/or an optical sensor. The thermofilament anemometry sensor can have a sensor element, e.g. a wire, wherein the sensor element can be electrically heated and its electrical resistance is a function of the temperature. A heat transfer into the fluid can take place as a result of the flow pattern, said heat transfer changing with the flow velocity. By measuring the electrical variables, the flow velocity can thus be deduced.

The determination appliance can also have a pressure sensor device with at least one differential pressure sensor and/or two barometric pressure sensors, wherein the pressure sensor device can in particular be designed to detect a pressure difference between two sensor points on two opposite sides of the blade wheel and to provide or send it to the determination device. A current pressure difference can thus be taken into account to determine the viscosity.

It is furthermore advantageous for the determination appliance to have a drive device, coupled or couplable to the blade wheel, for driving the blade wheel, wherein the determination device can in particular be designed to determine the viscosity by using a drive parameter of the drive device and/or of the blade wheel. In this case, the determination device can be designed to determine the viscosity by using a drive parameter of the drive device and/or of the blade wheel during operation of the drive device and/or of the blade wheel. The drive parameter can be understood to be an electrical power consumption of the drive device and/or a rotational speed and/or an angular speed of the blade wheel. Such a determination appliance can be formed or usable as a heart support system. This heart support system can advantageously determine a current blood viscosity and, for example, provide or send it for a diagnostic method.

Furthermore, a method for determining a viscosity of a fluid is presented. The method has a step of determining and a step of providing. In the step of determining, the viscosity of the fluid is determined by using at least one detected volume flow of the fluid and a detected pressure difference of the fluid. In the step of providing, a viscosity signal representing the viscosity determined in the step of determining is provided or sent.

This method can be carried out by using the previously presented determination appliance. The method can, for example, be implemented in software or hardware or in a mixed form of software and hardware in a control device, for example.

Advantageous is also a computer program product or computer program with program code which can be stored in a machine-readable carrier or storage medium, such as a semiconductor memory, a hard drive memory, or an optical memory, and is used to carry out, implement, and/or control the steps of the method, in particular when the program product or program is executed on a computer or an appliance.

BRIEF DESCRIPTION OF THE DRAWINGS

Exemplary embodiments of the approach presented here are shown in the drawings and explained in more detail in the following description. The figures show.

DETAILED DESCRIPTION

In the following description of favorable exemplary embodiments of the present approach, the same or similar reference signs are used for the elements that are shown in the various figures and have a similar effect, wherein a repeated description of these elements is omitted.

If an exemplary embodiment includes an "and/or" conjunction between a first feature and a second feature, this should be read to mean that the exemplary embodiment according to one embodiment comprises both the first feature and the second feature and according to another embodiment comprises either only the first feature or only the second feature.

Figure 1:
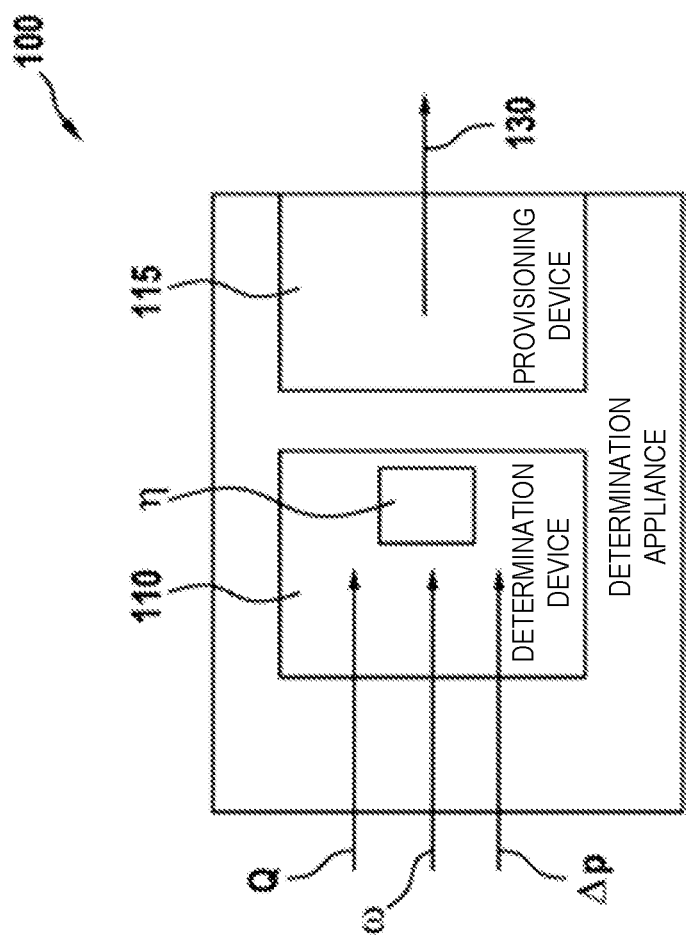
FIG. 1 a schematic illustration of a determination appliance for determining a viscosity of a fluid according to an exemplary embodiment.

FIG. 1 shows a schematic illustration of a determination appliance 100 for determining a viscosity $\eta$ of a fluid according to an exemplary embodiment.

The determination appliance 100 has a determination device 110 and a provisioning device 15. The determination device 110 is designed to determine the viscosity $\eta$ of the fluid by using at least one detected volume flow Q of the fluid and a detected pressure difference $\Delta p$ of the fluid. The provisioning device 115 is designed to provide or send a viscosity signal 130 representing the viscosity $\eta$ determined by the determination device 110. According to this exemplary embodiment, the determination device 110 is designed to read the detected volume flow Q and the detected pressure difference $\Delta p$ in the form of sensor signals.

Figure 2:
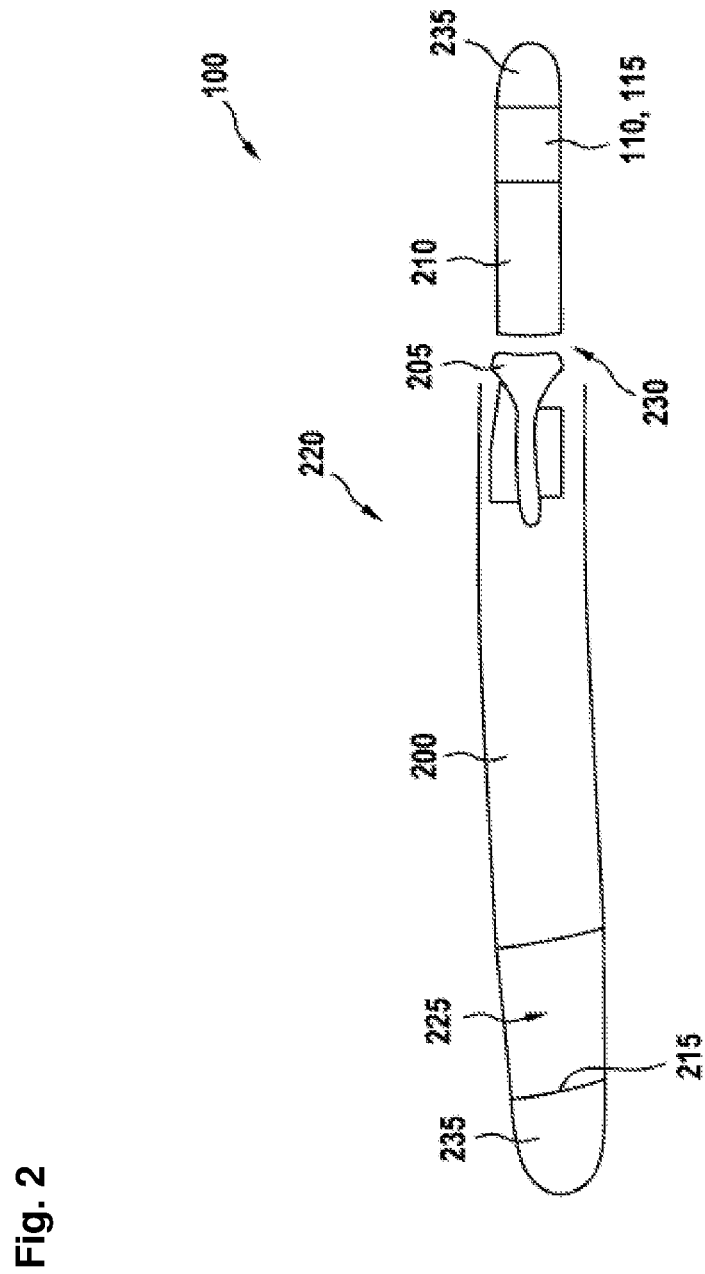
FIG. 2 a schematic side view of a determination appliance according to an exemplary embodiment.

FIG. 2 shows a schematic side view of a determination appliance 100 according to an exemplary embodiment. This determination appliance can be the determination appliance 100 described with reference to FIG. 1, with the difference that the determination appliance 100 according to this exemplary embodiment additionally has a cannula 200, a blade wheel 205, a drive device 210, a volume flow sensor 215, and a pressure sensor device 220.

The determination appliance or a determination device 110 can be integrated into the pump or arranged outside the body of a patient when no or only little installation space is available for microelectronic elements for measuring parameters that are required to determine the viscosity. In this case, for example, the electronics or corresponding components of the determination device 110 can be accommodated in a remote (implanted) control device so that predominantly a pressure sensor and/or a transducer element of the volume flow sensor can then be accommodated in the pump itself or implanted in the patient. The sensor values of the corresponding sensor(s) implanted in the patient can then be transmitted out of the patient wirelessly or by means of a signal line and processed in the determination device 110, for example, in a bag or on a belt of the patient, in order to determine the viscosity of the fluid (in this case, blood). Such an exemplary embodiment is not explicitly shown in the figures appended here.

Additionally or alternatively, the viscosity of the fluid can of course also be determined by means of a determination device 110 in the form of a cloud server, so that in this case, the sensor values required for the determination are to be transmitted via the internet or a corresponding signal line. An appropriate protection or encryption of this data against unauthorized tapping or reading of this data by unauthorized persons should advantageously be ensured in this case.

An arrangement of the determination device 110 in three options is thus conceivable:
1) Calculation of the viscosity by a determination device 110 implanted in the patient (e.g. as a control device or also in a pump, especially when corresponding hardware components have sufficiently small dimensions)
2) Extracorporeal calculation of the viscosity, e.g. close to the body of the patient (e.g. in a box attached to a belt of the patient)
3) Calculation of the viscosity further away from the patient (e.g. in a non-portable component, such as a tabletop device, an analysis device in a medical practice, or even a cloud server).

The cannula 200 has a receiving interface 225 formed to receive the fluid and a discharge interface 230 opposite the receiving interface 225 formed to discharge the fluid.

The blade wheel 205 is designed to convey the fluid from the receiving interface 225 to the discharge interface 230 of the cannula 200. According to this exemplary embodiment, the blade wheel 205 is arranged in the region of the discharge interface 230 and/or in the cannula 200.

The volume flow sensor 215 is designed to detect a volume flow of the fluid through the cannula 200 and to provide or send it to the determination device 110. Accordingly, the volume flow represents a volume flow of the fluid through the cannula 200. According to this embodiment example, the volume flow sensor 215 is arranged in the region of the receiving interface 225 for this purpose. According to this exemplary embodiment, the volume flow sensor 215 has a Doppler sensor. According to an alternative exemplary embodiment, the volume flow sensor 215 additionally or alternatively has a thermofilament anemometry sensor and/or an optical sensor.

According to this exemplary embodiment, the pressure sensor device 220 has two barometric pressure sensors 235, which are designed to detect a pressure difference between two sensor points on two opposite sides of the blade wheel 205 and to provide or send it to the determination device 110. According to an alternative exemplary embodiment, the pressure sensor device 220 additionally or alternatively has at least one differential pressure sensor. According to this exemplary embodiment, the pressure sensors 235 are arranged in the region of the receiving interface 225 and in the region of the discharge interface 230. Accordingly, the pressure difference according to this exemplary embodiment represents a difference between a pressure of the fluid in the region of the receiving interface 225 and a further pressure of the fluid in the region of the discharge interface 230.

The drive device 210 is coupled to the blade wheel 205 and designed to drive the blade wheel 205. According to this exemplary embodiment, the determination device 110 is designed to determine the viscosity by using a drive parameter of the drive device 210 and/or of the blade wheel 205 during operation of the drive device 210 and/or of the blade wheel 205.

In this case, the determination device 110 can, for example, be arranged outside the patient or a pump, e.g. in a portable control device. Sensor values of sensors implanted in the patient can then, for example, be supplied wirelessly or by means of a signal line to the determination device 110.

In the following, details of the determination appliance 100 are described again in more detail and in other words:

According to this exemplary embodiment, the determination appliance 100 presented here can be used as a heart support system. For patients with a heart support system, also called VAD patients (VAD stands for "Ventricular Assist Device"), coagulation management is essential for minimizing pump thromboses. For this purpose, patients are, for example, treated with medications to inhibit plasmatic blood coagulation, and the INR is adjusted in the range of 2 to 2.5, for example.

A mechanical load on the drive device 210 of a VAD system, i.e. of a heart support system, is a function of the volume flow, the pressure difference, and the viscosity. With a known volume flow and known pressure difference, which are measured in the determination appliance 100 presented here via sensors 215, 220, the viscosity of the fluid, in this case blood, can be deduced from the electrical power consumption of the drive device 210. For this purpose, the determination device 110 according to this exemplary embodiment is designed to read as the drive parameter a parameter which represents or makes it possible to determine the mechanical load on the drive device 210 and/or on the blade wheel 205. In this case, the determination device 110 is advantageously designed to divide the power consumption of the pump, consisting of the drive device 210 and the blade wheel 205, into a volume flow contribution and a viscosity contribution. The flow measurement is realized on the basis of ultrasound according to this exemplary embodiment or anemometrically according to an alternative exemplary embodiment. A direct determination of the viscosity during the operation of the determination appliance 100 is advantageously possible in this case by means of an explicit Doppler ultrasonic volume flow measurement. Advantageously, a pumping performance of the pump does not have to be interrupted for this purpose.

The blood viscosity is determined during operation of the determination appliance 100 by the determination device 110 continuously according to this exemplary embodiment or in fixed time intervals according to an alternative exemplary embodiment. The provisioning device 115 is designed to provide the determined viscosity to a physician and/or patient as a parameter for carrying out the treatment. For this purpose, the viscosity signal is designed to display the viscosity on a display and/or transmit it by radio transmission to a web service. As already stated above, the determination device 110 can also be arranged outside the patient, e.g. in a bag that the patient carries along. Signal values of sensors implanted in the patient can then, for example, be transmitted to the determination appliance wirelessly and/or by means of a signal line.

A determination appliance 100 presented here contains a system consisting of a pump drive in the form of the drive device 210, the blade wheel 205, and the cannula 200 also called the inlet cannula, the volume flow sensor 215 for measuring the pump volume flow actually conveyed by the drive and the blade wheel 205, in this case, by means of Doppler ultrasound, optionally or additionally by means of thermofilament anemometry and/or optical methods. An integration of the volume flow sensor 215 in the form of a Doppler ultrasonic sensor in a tip of the inlet cannula is shown here. In addition, the determination appliance 100 comprises two barometric pressure sensors 235 for forming the pressure difference in the determination device 110, which, according to this exemplary embodiment, has a data processing device in the form of a microcontroller. According to an alternative exemplary embodiment, the determination appliance 100 has at least one differential pressure sensor for determining a pressure gradient across the blade wheel 205 in the form of an impeller.

Figure 3:
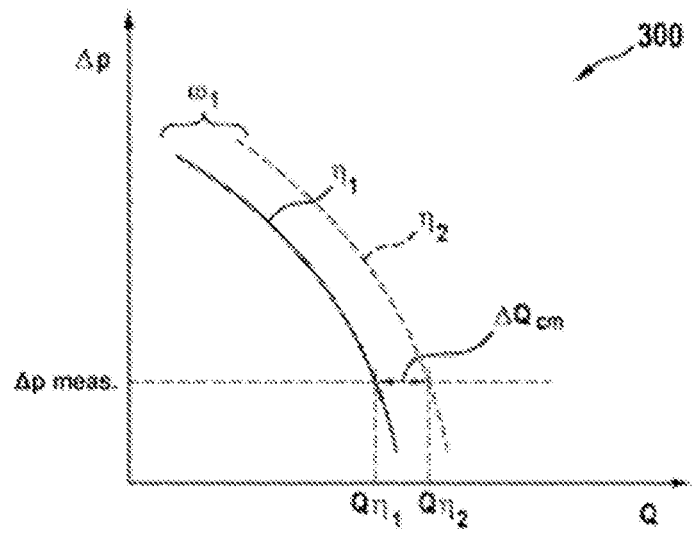
FIG. 3 a characteristic map of pressure difference over volume flow for various viscosities for use with a determination appliance according to an exemplary embodiment.

Calculation examples follow for illustrating possible methods of the determination device 110 when determining the viscosity, see also FIG. 3 in this respect:

The hydraulic power of the pump $P_{hydraulic}$ is a function of an angular speed ω, a hydraulic efficiency $\eta_{hydraulic}$, and a load torque M, wherein the load torque M is a function of the viscosity. This relationship can be represented in the following equation:

$$P_{hydraulic} = \omega \cdot M \cdot \eta_{hydraulic}$$

The hydraulic performance $P_{hydraulic}$ is also a function of the pressure difference Δp and the volume flow Q or volumetric flow. This relationship can be represented in the following equation:

$$P_{hydraulic} = \Delta p \cdot Q$$

If the pump is now operated at a defined angular speed ω1 and the actual volume flow $Q_{\omega 1}$ is measured, the viscosity η can be determined, as illustrated in FIG. 3, from this measured volume flow $Q_{\omega 1}$, according to this exemplary embodiment by means of Doppler ultrasonic sensors. For this purpose, according to this exemplary embodiment, a calibration of the measurement was carried out in advance such that both the viscosity varies in the relevant range and the rotational speed varies in the relevant range, and the resulting pump flows were measured. From this, "lookup tables," or LUT for short, were then created, with the help of which a viscosity can then be assigned by the determination device 110 to a measured pressure difference and a measured volume flow at a given rotational speed/angular speed. This measurement and calibration was carried out according to this exemplary embodiment by using the determination appliance 100. According to an alternative exemplary embodiment, the viscosity is determined by the determination device 110 by determining on the basis of the calibration values a functional relationship in the form of an empirical function, with the help of which the viscosity can subsequently be calculated:

$$\eta = f(\Delta p, Q, \omega)$$

As an alternative to the use of the angular speed ω, the electrical power consumption is used for the calculation by the determination device 110 according to an alternative exemplary embodiment, because:

$$P_{el} = P_{hyd} / (\eta_{el} \cdot \eta_{mech} \cdot \eta_{hyd})$$

This was determined in preliminary tests by measuring the torque and the rotational speed as well as the voltage U and current I by using the determination appliance 100. Under the premise that the further mechanical losses are only a function of the rotational speed and pressure, which is true in a very good approximation in the case of one of the determination appliances 100 presented here, it can be assumed that $\eta_{mech}$ is constant and therefore does not play a role in the viscosity determination.

The volume flow sensor 215 can be proven optically or by fluoroscopy. The calculation of the viscosity from the pressure difference, volume flow, and/or angular speed can be proven in a purposeful experiment by manipulating the volume flow or the pressure difference.

FIG. 3 shows a characteristic map 300 of pressure difference Δp over volume flow Q for various viscosities η for use with a determination appliance according to an exemplary embodiment. This determination appliance can be one of the determination appliances 100 described in FIG. 1 or 2. According to this exemplary embodiment, the characteristic map 300 is stored in the form of the lookup table described in FIG. 2 or the functional relationship in the determination device of the determination appliance or can be read by the determination device.

For $\Delta p_{meas} =$, it follows that $$Q = f(\eta) \text{ where } Q_{\eta 2} > Q_{\eta 1} \text{ for } \eta_1 > \eta_2.$$

Figure 4:
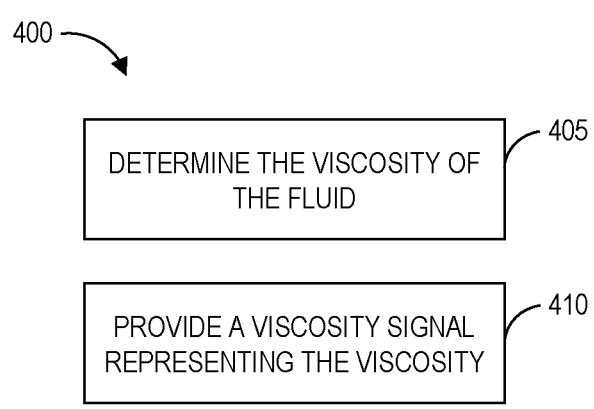
FIG. 4 a flow diagram of a method for determining a viscosity of a fluid according to an exemplary embodiment.

FIG. 4 shows a flow diagram of a method 400 for determining a viscosity of a fluid according to an exemplary embodiment. This method can be a method 400 that can be carried out or controlled by one of the determination appliances described with reference to one of FIG. 1 or 2.

The method 400 has a step 405 of determining and a step 410 of providing. In step 405 of determining, the viscosity of the fluid is determined by using at least one detected volume flow 10 of the fluid and a detected pressure difference of the fluid and/or a rotational speed of a blade wheel for conveying the fluid. In the step 410 of providing, a viscosity signal representing the viscosity determined in the step 405 of determining is provided or sent.

The method steps presented here can be repeated as well as carried out in a sequence other than the one described.

The invention claimed is:

1. A ventricular assist system comprising:
   an impeller;
   a drive device coupled to the impeller, the drive device configured to drive the impeller at a rotational speed (ω);
   a pressure sensor device; and
   a determination device comprising:
      a cannula configured to be implanted in a body of a patient, wherein the cannula comprises:
         a lateral receiving interface distal to the impeller, configured to receive blood of the patient into an interior of the cannula; and
         an outlet interface, wherein the impeller is configured to convey the blood from the lateral receiving interface to the outlet interface; and
      a volumetric flow sensor positioned at a tip of the cannula distal to the impeller and configured to sense a volumetric flow (Q) of the blood of the patient through the cannula, the volumetric flow sensor comprising a Doppler ultrasonic sensor;
   wherein the pressure sensor device is configured to sense a pressure difference (Δp) of the blood in a region of the receiving interface and a region of the outlet interface, and
   wherein the determination device is configured to determine viscosity (η) of blood in the body of the patient based on at least the sensed volumetric flow (Q) of the blood, the sensed pressure difference (Δp) of the blood, and either the rotational speed (ω) of the impeller or an electric power input $P_{el}$ of a drive device for the impeller.

2. The ventricular assist system of claim 1, wherein the determination device is configured to determine the viscosity (η) based on a functional relationship between the volumetric flow (Q), the pressure difference (Δp), and the viscosity (η).

3. The ventricular assist system of claim 1, wherein the determination device is configured to determine the viscosity (η) using a lookup table.

4. The ventricular assist system of claim 3, wherein a relationship between the volumetric flow (Q), the pressure difference (Δp), and the viscosity (η) is stored in the lookup table.

5. The ventricular assist system of claim 1, wherein the impeller is positioned in a region of the outlet interface.

6. The ventricular assist system of claim 1, wherein the pressure sensor device comprises at least one differential pressure sensor or two barometric pressure sensors, wherein the at least one differential pressure sensor or two barometric pressure sensors are configured to measure the pressure difference ($\Delta p$) between two sensor points.

7. The ventricular assist system of claim 1, wherein the pressure sensor device is configured to sense the pressure difference ($\Delta p$) between two sensor points.

8. A method for determining a viscosity ($\eta$) of blood of a patient in a ventricular assist system, comprising:
  sensing a volumetric flow (Q) using a volumetric flow sensor of a determination device of the ventricular assist system, the volumetric flow sensor comprising a Doppler ultrasonic sensor arranged in a distal tip of a cannula of the determination device, the cannula, configured to be implanted in a body of the patient, wherein the ventricular assist system comprises:
    an impeller configured to convey blood from a lateral receiving interface of the cannula distal to the impeller to an outlet interface of the cannula; and
    a drive device coupled to the impeller, the drive device configured to drive the impeller at a rotational speed ($\omega$);
  sensing a pressure difference ($\Delta p$) of blood in a region of the receiving interface and the outlet interface; and
  determining the viscosity ($\eta$) of the blood based on at least the sensed volumetric flow (Q) of the blood, the sensed pressure difference ($\Delta p$) of the blood, and either the rotational speed ($\omega$) of the impeller or an electric power input $P_{el}$ of a drive device for the impeller.

9. The method of claim 8, wherein determining the viscosity ($\eta$) comprises determining the viscosity ($\eta$) based on a functional relationship between the volumetric flow (Q), the pressure difference ($\Delta p$), and the viscosity ($\eta$).

10. The method of claim 8, wherein determining the viscosity ($\eta$) comprises using a lookup table.

11. The method of claim 10, wherein a relationship between the volumetric flow (Q), the pressure difference ($\Delta p$), and the viscosity ($\eta$) is stored in the lookup table.

12. The method of claim 8, wherein the impeller is positioned in a region of the outlet interface.

13. The method of claim 8, wherein the pressure sensor device comprises at least one differential pressure sensor or two barometric pressure sensors.

14. The method of claim 8, wherein the pressure sensor device is configured to sense a pressure difference ($\Delta p$) between two sensor points.

15. A non-transitory computer-readable storage medium comprising instructions that, when executed, direct a processor to perform a method comprising:
  sensing a volumetric flow (Q) using a volumetric flow sensor of a determination device of a ventricular assist system, the volumetric flow sensor comprising a Doppler ultrasonic sensor arranged in a distal tip of a cannula of the determination device, the cannula, configured to be implanted in a body of a patient, wherein the ventricular assist system comprises:
    an impeller configured to convey blood from a lateral receiving interface of the cannula that is distal to the impeller to an outlet interface of the cannula; and
    a drive device coupled to the impeller, the drive device configured to drive the impeller at a rotational speed ($\omega$);
  sensing a pressure difference ($\Delta p$) of blood in a region of the receiving interface and the outlet interface; and
  determining a viscosity ($\eta$) of the blood based on at least the sensed volumetric flow (Q) of the blood, the sensed pressure difference ($\Delta p$) of the blood, and either the rotational speed (co) of the impeller or an electric power input $P_{el}$ of a drive device for the impeller.

16. The non-transitory computer-readable storage medium of claim 15, wherein determining the viscosity ($\eta$) comprises determining the viscosity ($\eta$) based on a functional relationship between the volumetric flow (Q), the pressure difference ($\Delta p$), and the viscosity ($\eta$).

17. The non-transitory computer-readable storage medium of claim 15, wherein determining the viscosity ($\eta$) comprises using a lookup table.

18. The non-transitory computer-readable storage medium of claim 17, wherein a relationship between the volumetric flow (Q), the pressure difference ($\Delta p$), and the viscosity ($\eta$) is stored in the lookup table.

\* \* \* \* \*